United States Patent [19]

Gregory

[11] 4,036,213
[45] July 19, 1977

[54] PROCESS FOR DETERMINING VERTEBRAE LOCATIONS IN HUMANS

[75] Inventor: Ralph R. Gregory, Monroe, Mich.

[73] Assignee: National Upper Cervical Chiropractic Research Association, Inc., Monroe, Mich.

[21] Appl. No.: 682,519

[22] Filed: May 3, 1976

[51] Int. Cl.² .............................................. A61B 5/10
[52] U.S. Cl. .................................. 128/2 S; 33/174 D
[58] Field of Search ...................... 128/2 S; 33/174 D

[56] References Cited

U.S. PATENT DOCUMENTS

| 2,111,648 | 3/1938 | Stone ................................... 33/174 D |
| 2,324,672 | 7/1943 | Bierman et al. ................... 128/2 S X |
| 2,810,964 | 10/1957 | Engelbert ........................... 33/174 D |
| 2,930,133 | 3/1960 | Thompson ......................... 33/174 D |
| 3,336,917 | 8/1967 | Pile et al. .............................. 128/2 S |
| 3,955,285 | 5/1976 | Moecl ................................. 33/174 D |

*Primary Examiner*—Kyle L. Howell
*Attorney, Agent, or Firm*—Harness, Dickey & Pierce

[57] ABSTRACT

The process of the present invention comprises the steps of, and means for, determining the location of vertebrae in the human spine relative to each other. The process establishes accurately the location of the atlas vertebra in all of its planes in relationship to the occiput and subjacent vertebrae including specifically the dorsal vertebrae and pelvis. The process is useful in the determinaion of, and correction of, any misalignment of the atlas vertebra, the head and/or pelvis and their supporting spinal vertebrae.

2 Claims, 3 Drawing Figures

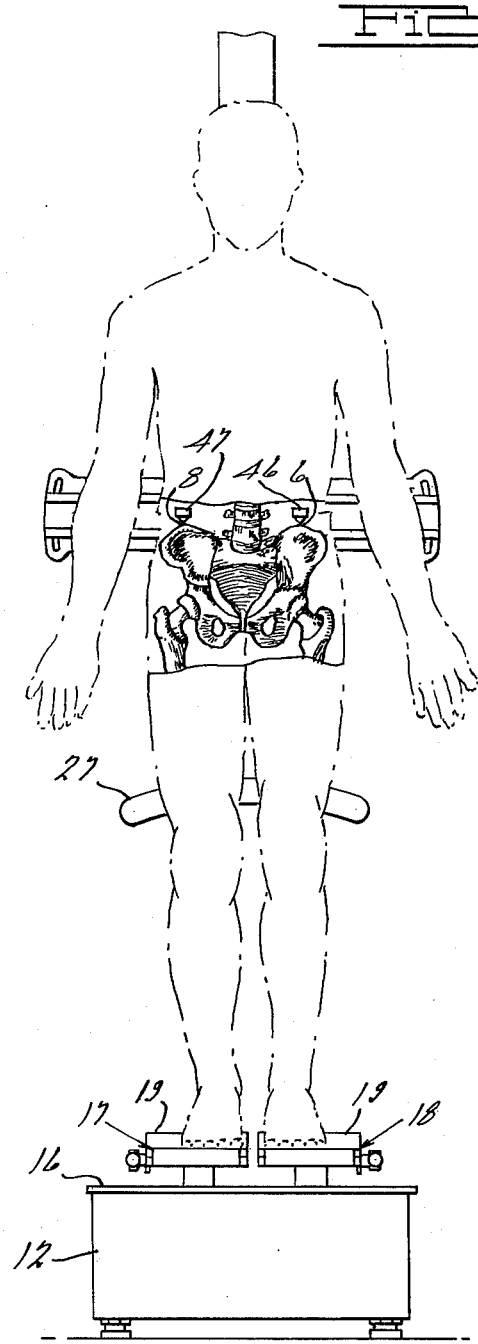
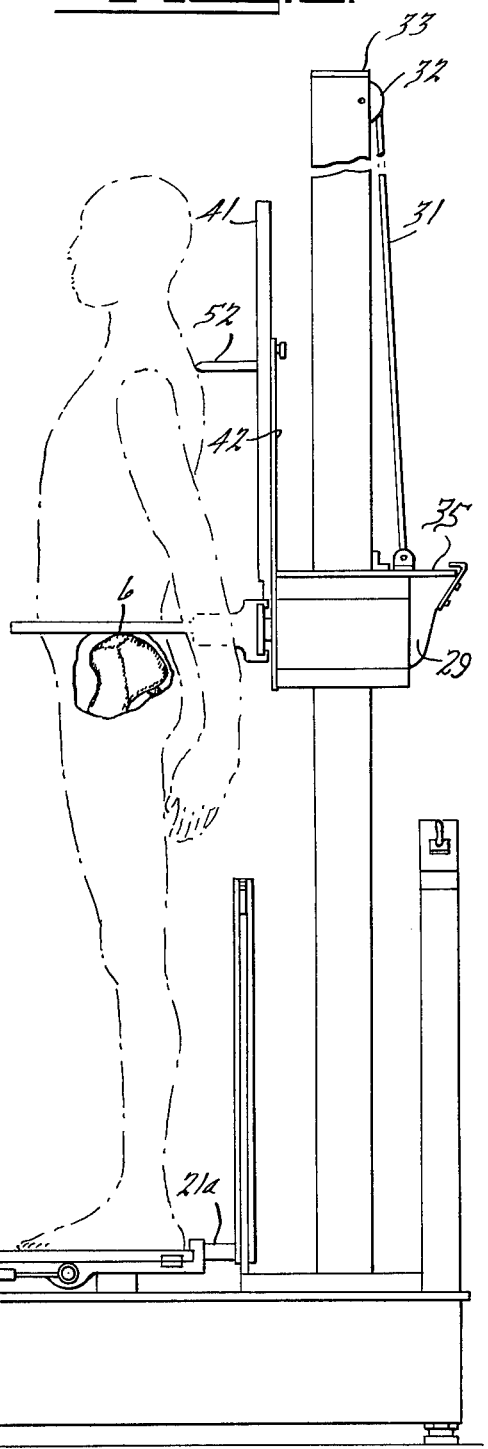

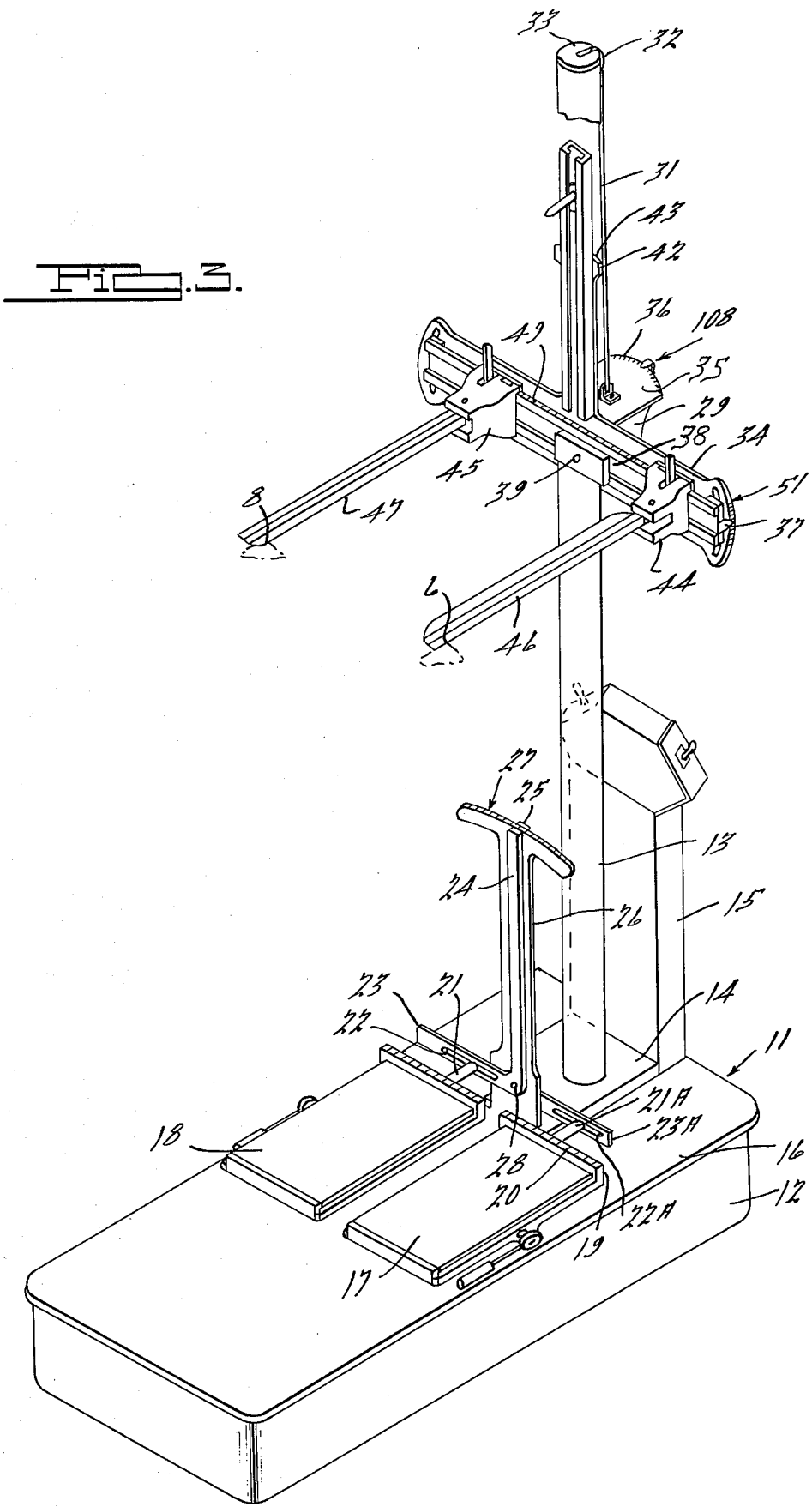

PROCESS FOR DETERMINING VERTEBRAE LOCATIONS IN HUMANS

BACKGROUND OF THE INVENTION

The orthodox premise of chiropractic practice is defined as the correction, restoration toward normal, or replacement of misalignments of subluxated vertebrae by the act of adjusting such subluxated vertebrae to their normal, relative position. A subluxation is a condition caused by vertebrae misalignments. A subluxation results from the abnormal movement of subluxated vertebra, which through pressure, or interference of an irritation producing mechanism detrimentally affects the nervous system, specifically the spinal cord which is lodged in the vertebral canal, and can cause abnormal functioning of the central nervous system which manifests itself in a variety of conditions and/or diseases in humans.

The process of the present invention is based on the premise that the atlas vertebra also known as "C-1", that is, the uppermost vertebra of the human spine which supports the skull is the most important vertebra in the spinal column because of its proximity to the caudal region of the brain stem.

Observations in a large number of cases have shown that pelvic distortion is accompanied by, and correlates with, some misalignment in the C-1 vertebrae, in one or more planes or its positional relationship to the occiput. It is desirable to be able to quickly, accurately, and reproducibly, determine this information.

It has long been known to chiropractors that it is important to correct occiputal-atlanto-axial subluxations. Typically, in the past, correction of such subluxations has been accomplished by using X-rays as the primary source of information as to the location of C-1, subjacent vertebrae and the positional relationship of C-1 to the occiput. In the prior normal routine, a series of X-rays were taken in the three planes of motion in which spinal vertebrae can abnormally move and a listing prepared from an analysis of the degrees of abnormal motion. After adjustment, a second series of X-ryas were taken and an appraisal made of the degree of correction of the misalignments.

Generally stated, this invention provides a process which provides vertebrae location information that is useful to chiropractor in determining the absence or presence of nerve pressure caused by a subluxated atlas. This information comprises measurements of bodily distortion including distortion of the pelvis, vertebrae in the lumbosacral region or other portions of the spinal column, and distortion of the spinal column as a whole. Such information is indicative of distortion, or imbalance in the reticular formation of the brain stem which causes spastic contracture in the skeletal muscles.

A process which enables the determinations of distortions of vertebrae subjacent to the atlas, by procedures and means other than X-ray, and which provides accurate information as to the the effects of an atlas adjustment, or the need for further adjustment. Such procedures in addition to providing a fast and inexpensive method of determining the desired vertebrae locations also eliminates the necessity for repeat X-ray determinations and thereby reduces exposure to X-rays.

BRIEF DESCRIPTION OF THE DRAWINGS

FIG. 1 is a front view of a machine with an occupant thereon which practices the method of the present invention;

FIG. 2 is a side view of the structure illustrated in FIG. 1, and

FIG. 3 is a perspective view of the machine illustrated in FIGS. 1 and 2.

DETAILED DESCRIPTION OF THE INVENTION

The process of this invention involves the determination of data about the atlas vertebra and the immediately subjacent vertebrae in the cervical spine, i.e., the first seven vertebrae designated C-1 - C-7, inclusive, and recording the position thus determined for, particularly the atlas vertebra, in each of the three planes of possible movement, namely, the frontal, sagittal and transverse planes. This determination is accomplished by using X-rays with proper alignment and adjustments to insure accuracy of interpretation of X-rays in each of the three planes to enable the degrees of inclination to be accurately observed and recorded. Such X-rays provide the exact location of atlas vertebra in each of the lateral, sagittal and transverse planes and determine its positional relationship to the occiput and to subjacent vertebral segments. Additional information as to the location of the dorsal vertebrae, particularly the first and second vertebra at the upper end of the chest cavity and including the first thoracic vertebra are determined for any deviation from the vertical axis, that is, the vertical line of intersection of the frontal and sagittal planes which bisect the human body at right angles. The frontal plane is the plane which bisects the body of a human in the standing position that includes both of the shoulder bones and each ilium. The sagittal plane bisects the spine and the skull at right angles to the frontal plane.

A determination of the distortions in the lumbosacral area is made by determining deviations which may exist from the axes of the frontal and sagittal planes of the pelvic girdle. Specifically, a measurement is made of such deviations by positioning a human in a standing position on separate support surfaces for each foot and while the human is standing in an erect position, as nearly vertical as possible, the distance between the uppermost poriton of each ilium is measured. For the purpose of determining an accurate deviation of the uppermost portion of each ilium from the axes of the frontal and sagittal planes, it is important to insure that the spacing of the feet is such that the weight of the body is carried on points immediately below the uppermost point of each ilium. An adjustment to insure such a condition is made by carefully positioning the center porton of each heel bone at a spacing such that the width between the heel bones is identical to the width between the uppermost portion of each ilium. Measurements are then made to determine whether the uppermost portion of each ilium lies in a single horizontal plane, or deviates therefrom. A separate determination is made as to whether the uppermost part of each ilium lies in a frontal plane which is at right angles to the sagittal plane and any deviation therefrom is recorded. Such deviation actually constitutes a rotation of the plane of the uppermost part of each ilium. In those instances in which the uppermost part of each ilium deviates from the axes of either of the frontal or sagittal plane, an adjustment is made to raise or lower one or both of the feet. This is accomplished by elevating the support surface for, usually, the foot which is on the side of the ilium which is lowest and the elevation is continued until the uppermost point of each ilium lies in substantially the same horizontal plane. Relative adjustment of the level of the support for each foot is continued until the uppermost part of each ilium lies in the same horizontal plane and simultaneously lies in the same sagittal plane. The relative horizontal position of each foot support is recorded and becomes a portion of the basis for later comparisons of measurements made on the same human at a later time.

When the above measurements have been made, and an adjustment is made to the atlas vertebrae, a post measurement is taken to determine whether a distortion of the pelvis still exists. This determination is made by positioning each foot on supports which lie in the same horizontal plane and determining the location of the uppermost part of each ilium relative to the vertical axis, i.e., the axes of the frontal and sagittal planes and making a comparison between the locations so determined and the locations determined prior to the adjustment of the atlas vertebrae.

The process of this invention is useful for checking the degree of correction of spastic contracture resulting from an atlas adjustment shortly after the adjustment is made; in a similar manner, it is particularly useful in checking for pelvic distortion with the passage of time after an adjustment without repeat X-rays. For such later checking purposes, the process involves the determination of the relative location of the vertebrae in the lumbosacral region and the pelvic girdle for a human previously measured, and/or atlas vertebrae adjusted, by positioning such human in a standing position on support surfaces for each foot in the same horizontal plane and then determining the precise location of the uppermost point of each ilium relative to the axes of the frontal and sagittal planes. In those instances in which such determination reveals that the location of the uppermost point of each ilium is unchanged, or so modified as to exhibit less deviation from the axes of the frontal and/or sagittal planes, than the previously recorded deviation, the effect of the atlas vertebrae adjustment and the permanent nature thereof is thus easily and quickly evaluated without the necessity of resorting to additional X-rays to actually inspect the location of that atlas vertebrae in each of the frontal, sagittal and transverse planes.

The determinations of the deviation of the uppermost part of each ilium from the axes of the frontal and sagittal planes may be accomplished in any of a number of ways and with any means which are capable of precisly measuring the width between the uppermost points of each ilium such that the width of the spacing between the heels can be accurately accomplished. Such means must provide separate vertically adjustable support surfaces for each foot and means for determining the degree of slant of the imaginary plane tangent to the uppermost points on eac ilium and the imaginary plane which is at right angles thereto. For purposes of further clarification, the process of this invention will now be described in conjunction with one specific apparatus which has been found to be suitable for satisfactory performance of the process of this invention. This apparatus is the subject matter of copending application Ser. No. 682,518, filed concurrently herewith as the invention of Ralph R. Gregory and Peter Benesh, which is entitled "A Machine for Determining Vertebrae Locations in the Human Body."

The apparatus illustrated in FIG. 3 comprises a machine generally designated 11 having a base 12 from which a vertically extending column 13 is suppoted and reinforced by a plate 14 which engages an upright pedestal 15. The top plate 16 is secured to the top of the base 12 and a pair of platforms 17 and 18 are disposed thereabove for individual movement up and down in the vertical plane by means not shown. The platforms 17 and 18 are separate supporting surfaces for each foot of a human and as there shown, each platform is provided with a flange 19, the upper surface of which is graduated at 20, so as to enable positioning of the center bone of the heel thereon in locations at predetermined width spacings. The relative location in the horizontal plane of the upper surfaces of platforms 17 and 18 are indicated on the scale 27 mounted on vertical plate 26. The location of platform 18 is indicated through motion of the upstanding arm portion 24 pivotally attached to plate 26 by pivot means 28 and actuated by the rod 21 sliding in slot 22 in the horizontal porton 23. The relative height of supporting platform 17 is indicated by the relative position of the corresponding upstanding arm 25 which is actuated by rod 21A which extends into a corresponding slot 22A in the horizontal portion 23A.

Vertically adjustable, rotationally mounted and pivotally movable means for determining the spacial location of the uppermost part of each ilium is mounted on upstanding column 13. Cylindrical sleeve 29 surrounds column 13 and is counter-balanced by a cable 31 supported on column 13, which cable extends over a counter-balancing wheel 32 which is secured to a weight (not illustrated within the column). Wheel 32 is mounted on a cap 33 located in the top area of column 13. A pair of arms 46, 47, are pivotally mounted on housings 44, 45, respectively. Housing 44 and 45 are mounted on a cross bar 38 which is attached to fixed plate 34 which is directly secured to sleeve 29 and, therefore, moves vertically And angularly as sleeve 29 is raised or lowered, or rotates around column 13. Transverse plate 35 is secured to one end of cable 31 and is arranged for a vertical sliding motion in fixed relationship to column 13 as plate 35 moves upwardly and downwardly. Arms 46 and 47 are slidably mounted on plate 38 which is pivotally carried on pivot 39 and positioned adjacent to fixed plate 35 for angular movement relative thereto as indicated by indicator 37 relative to the graduated markings 51 on the end of fixed plate 34. Arms 46 and 47 are used in the process of this invention, first, to measure the width between each ilium of the human being measured. Arm 46 is moved inwardly until the middle portion of its lower surface is directly in contact with the uppermost portion of the ilium 6. Arm 47 is moved to the position such that the middle of its lower surface is in direct contact of its uppermost portion 8 of the other ilium. The distance between arms 46 and 47 are noted on scale 49 and an adjustment is made by positioning each heel on support platforms 17 and 18 so as to be located directly beneath the corresponding ilium to thereby insure the exact width spacing between the heels as the width between the uppermost point of each ilium 6 and 8. With the heels thus positioned, readings are taken of any rotation of the arm 38 in the vertical plane as indicated on scale 51 and any rotation of sleeve 29 relative to fixed column 13 as indicated by indicator 108 is also recorded. The observation on indicator scale 51 measures the deviation of the plane of the uppermost point of each ilium from the horizonatal while the reading obtained on plate 35 represents the deviation of the pelvic girdle, as indicated by the place of the uppermost points of each ilium about the axis of the sagittal plane, or otherwise expressed into the canted transverse plane defined by the lower surface of each of the arms 46 and 47.

For the purpose of determining whether any deviation of the uppermost parts of each ilium in the vertical plane or rotationally with respect to the sagittal plane, the level of the surface supporting one of the feet is changed and observations made with respect to whether such change causes modification of the deviation readings previously taken. Usually, the support surface for the foot which is on the side of the arm 46 or 47 which is the lowest, is raised until the scale reading on scale 51 is 0 and, similarly, the scale reading on scale 36 is 0. When the scale 51 and scale 36 readings are 0 the height of the support surface 17 or 18, as the case may be, is recorded for later reference in the event subsequent readings are made upon the same human.

Angular deviation of vertebrae in the upper cervical area, i.e., between the atlas vertebrae and the thoracic vertebra may be determined by vertebral probe 52 into direct contact with the particular vertebra to be checked. Vertebral probe 52 is carried by verteberal slide bar 41 which is secured for pivotal movement around pivot 39. With the uppermost portion of each ilium in the same horizontal plane and in the absence of rotation, vertebral probe 52 will indicate any angular variation from the vertical axis of the selected vertebrae on vertebral indicator 42 which is provided with a scale 43 on its upper angular surface.

It will be appreciated that the recorded deviations of the pelvic girdle region as above described can be readily repeated at any time it is desired to recheck the relative location of the vertebrae which have been previously determined and recorded by merely following the above described steps in the same order and under the same conditions as expressed. The process thus provides an easy, fast, inexpensive but reliable procedure for accurately determining the relative locations of key vertebrae in humans at any time such determination is desired and without the necessity for additional X-ray photographs in the various planes of possible motion of the atlas vertebrae.

What is claimed is:

1. A process for determining the adjustment to be made to the vertebrae in the human spine which comprises the steps of (1) establishing the location of the atlas vertebra in each of the lateral, sagittal and transverse planes, (2) positioning a human in a standing position on separate support surfaces for each foot, (3) determining the width of the uppermost part of each ilium and adjusting the spacing between the feet such that the width between the center of each heel is the same as the width between each said uppermost part of each ilium, (4) determining the deviation of the uppermost portion of each ilium from the axis of the lateral and sagittal planes, (5) adjusting the height of the plane upon which at least one foot is supported unti the uppermost portion of each ilium lies substantially in the same lateral plane and substantially in the same horizontal plane and recording any deviation therefrom (6) adjusting the location of the atlas vertebra, and (7) thereafter determining any deviation from the axis of the lateral and sagittal planes of each ilium when the support surfaces for each foot lie in the same horizontal plane.

2. A process for determining the adjustment to be made to the vertebrae in the human spine which comprises the steps of (1) positioning a human in a standing position on separate support surfaces for each foot, said support surfaces lying in the same horizontal plane, (2) determining the width of the uppermost part of each ili um and adjusting the spacing between the feet such that the width between the center of each heel is the same as the width between each said uppormost part of each ilium, and (3) determining any deviation of the uppermost portion of each ilium from the axis of the lateral and from the axis of the sagittal plane.

* * * * *